(12) United States Patent
Freed

(10) Patent No.: US 8,160,712 B1
(45) Date of Patent: Apr. 17, 2012

(54) APPARATUS AND METHOD FOR TREATING SLEEP APNEA

(76) Inventor: Marcy Freed, Tulalip, WA (US)

( * ) Notice: Subject to any disclaimer, the term of this patent is extended or adjusted under 35 U.S.C. 154(b) by 95 days.

(21) Appl. No.: 12/565,571

(22) Filed: Sep. 23, 2009

(51) Int. Cl.
*A61N 1/36* (2006.01)

(52) U.S. Cl. ........................................................ 607/42

(58) Field of Classification Search ................. 600/382, 600/386–394, 546, 554; 607/42
See application file for complete search history.

(56) References Cited

U.S. PATENT DOCUMENTS

| | | |
|---|---|---|
| 5,146,918 A | 9/1992 | Kallok et al. |
| 5,678,535 A | 10/1997 | DiMarco |
| 5,911,218 A | 6/1999 | DiMarco |
| 6,463,327 B1 * | 10/2002 | Lurie et al. ..................... 607/42 |
| 6,587,725 B1 | 7/2003 | Durand et al. |
| 6,587,727 B2 | 7/2003 | Osorio et al. |
| 6,770,022 B2 | 8/2004 | Mechlenburg et al. |
| 6,770,725 B2 | 8/2004 | Santerre |
| 7,082,331 B1 | 7/2006 | Park et al. |
| 7,177,691 B2 | 2/2007 | Meadows et al. |
| 7,245,971 B2 | 7/2007 | Park et al. |
| 7,277,749 B2 | 10/2007 | Gordon et al. |
| 2001/0010010 A1 | 7/2001 | Richmond et al. |
| 2002/0072781 A1 * | 6/2002 | Lattner et al. ................... 607/42 |
| 2002/0188332 A1 * | 12/2002 | Lurie et al. ..................... 607/48 |
| 2003/0093128 A1 * | 5/2003 | Freed et al. ..................... 607/42 |
| 2003/0153954 A1 | 8/2003 | Park et al. |
| 2003/0195571 A1 | 10/2003 | Burnes et al. |
| 2003/0216789 A1 | 11/2003 | Deem et al. |
| 2006/0224211 A1 | 10/2006 | Durand et al. |
| 2006/0276701 A1 | 12/2006 | Ray |
| 2008/0021506 A1 | 1/2008 | Grocela |
| 2008/0103545 A1 * | 5/2008 | Bolea et al. ..................... 607/42 |
| 2008/0109047 A1 | 5/2008 | Pless |
| 2008/0215106 A1 * | 9/2008 | Lee et al. ........................ 607/17 |

* cited by examiner

*Primary Examiner* — Carl H Layno
*Assistant Examiner* — Allen Porter, Jr.
(74) *Attorney, Agent, or Firm* — Dean Craine

(57) ABSTRACT

An apparatus and method for treating sleep apnea comprising an external, low voltage electrical stimulator that provides between 5 to 25 milliamps connected to electrodes imbedded located over the first and third intercostals or the third and fifth intercostals. The stimulator is designed to provide a current to the electrodes that stimulated one of the two pairs of intercostals for 59 seconds, rest for 4 seconds and then repeats the cycle throughout the night after the user has fallen asleep. The stimulator includes a main power switch and two amplitude control switches (also called amplitude control switches), a main control switch, an adustable delay activation timer switch, a power timer switch, an amplitude lock switch, two channel electrode wire plugs, an LCD display, and a battery pack. Prior to use, the amplitude control switches adjusted and lock at an amplitude needed to cause contraction. of the intercostals assigned to the channel. The patient then connects the electrode wires to the intercostals electrodes and activates the stimulator.

4 Claims, 6 Drawing Sheets

APPARATUS AND METHOD FOR TREATING SLEEP APNEA

Notice is hereby given that the following patent document contains original material which is subject to copyright protection. The copyright owner has no objection to the facsimile or digital download reproduction of all or part of the patent document, but otherwise reserves all copyrights whatsoever.

BACKGROUND OF THE INVENTION

1. Field of the Invention

The present invention pertains to medical apparatus and methods and more particularly, to apparatus and methods used for treating sleep apnea.

2. Description of the Related Art

Apnea is a common sleep disorder characterized by one or more pauses in breathing or shallow breaths while sleeping The breathing pauses can last from a few seconds to several minutes and can occur 5 to 30 times or more an hour. Typically, when breathing is resumed, a loud snort or choking sound occurs that is heard by others sleeping nearby. The sudden snort or choking sound often wakes up the individual and disrupts his or her sleeping cycles thereby causing the individual to feel physically and mentally tried the next morning. Severe sleep depredation is a major symptom found in patients suffering from sleep apnea.

There are two generally type of sleep apnea—obstructive sleep apnea (OSA) and central sleep apnea, (CSA). OSA is the most common and is believed to be caused by muscles in the throat that collapse and obstruct breathing. The method and apparatus disclosed in U.S. Pat. No. 6,587,725 is used to treat OSA. CSA is less common cause of sleep apnea and is believed to be caused by imbalances in the brain's respiratory control centers.

Recently, electrical stimulation to an individual's breathing muscles has been used to treat both OSA and CSA. Typically, sensors and stimulators have been surgically implanted into the diaphragm, neck muscles, the genioglossus and the phrenic nerve. The sensors are typically coupled via an external machine to activate the stimulators when a signal is received from the sensor. A stimulating stimulating current is then delivered to the upper respiratory muscles in the neck. Normally, the sensors monitor for breathing cessation, minute diaphragm contraction, high blood carbon dioxide levels EEG patterns, and EMG patterns. Controlling sleep apnea by the sensing and stimulating various respiratory muscles is disclosed in U.S. Pat. Nos. 6,587,727; 6,770,725; 5,678,535; 5,146,918 and U.S. Patent application 2008/0109047. One drawback with using imbedded sensors and stimulators is that they must be surgically mounted inside the body, and do not prevent the apnea episode. The patient's sleep is still disturbed.

Breathing machines, such as CPAP machines, are commonly used to treat OSC and CSA apnea. Such machines create continuous positive airway pressure from a shoe box size air pump that connects to a mask worn by the patient. The mask, also called the interface, normally includes head gear, a nose piece, a mouth pieces, and tubing. It is important that the head gear, the nose piece, and the mouth piece fit properly to provide a proper seal to deliver positive airflow. Finding a mask that meets these criteria that is comfortable when sleeping and is compatible with the patient's sleeping position (back sleeper, side sleeper, and abdomen sleeper) is difficult. Because the air pump is loud, and the mask is uncomfortable, most patients who use CPAP machines rarely have uninterrupted sleep.

What is needed is an improved apparatus and method for treating apnea that prevents apnea episodes from occurring during sleep, is small, quiet, comfortable to use.

SUMMARY OF THE INVENTION

The above stated needs are met by the apparatus and method for treating sleep apnea disclosed herein that comprises a low voltage, dual channel electrical stimulator that provides between 5 to 25 milliamps to a pair of electrodes externally mounted over one of two pairs of intercostals— either the first and third intercostals or the third and fifth intercostals. The stimulator includes a main power switch, a main power timer switch, two voltage or amplitude control switches, two channel electrode wire ports, two electrode wires each with a cathode connector and an anode connector, an LCD display, an adjustable delay activation switch, an amplitude lock switch and a battery pack.

Prior to use, two pairs of contact electrodes are precisely mounted over the first and third intercostals or the third and fifth intercostals on the right side of the patient's chest. During the initial evaluation, the electrical conduction and contraction properties of each intercostals is tested to determine the required amplitude (i.e. voltage) needed to cause contraction. When the correct amplitude is used, the patient will experience a slight 'pulling sensation' on the chest wall. Ideally, the amplitude should be sufficiently high enough to cause contraction but sufficient low to minimize the 'pulling sensation'. Which particular pair of intercostals used also depends on the patient's preferred sleeping position and turning habits.

Once the desired pair of intercostals have been selected, a channel on the stimulator is then assigned to one of the interscostals in the selected pair of intercostals. Prior to dispensing the device to the patient, the amplitude for each channel is then set and locked into the stimulator by the healthcare provider using the amplitude control switches and amplitude lock switch mounted on the stimulator. During use, the voltages or amplitudes assigned to the first and second channels are displayed on the LCD display along with amplitude lock or unlock symbols.

Prior to sleeping, an electrode wire is connected to each channel port on the stimulator. Each electrode wire includes a cathode connector and an anode connector. The patient then connects the cathode and anode connectors on each electrode wire to the electrodes located over the desired pair of intercostals. During setup, the patient also determines the duration of the sleep period (1, 2, 4, 6 or 8 hrs) and sets the main power timer switch to the sleep period so that the stimulator operates continuously throughout the sleep period. The patient also adjusts the delay activation switch to set the time the stimulator begins to created pulses. The main power timer switch is then activated.

In the preferred embodiment, the stimulator is designed to provide an electric current (5 to 25 milliamps) in 700 microseconds pulses (biphasic symmetrical and square) with two stimulation phases each lasting approximately 300 microseconds separated by an interphase lasting approximately 100 microseconds. The stimulator then continuous provides pulses for 59 seconds and then rests for 4 seconds. The stimulation cycle of 59 seconds ON and 4 seconds OFF is repeated throughout the sleeping period. As mentioned above, the stimulator includes a delay feature that allows the patient to select a time period before the first stimulation cycle begins so that the patient may fall into deep sleep.

DESCRIPTION OF THE PREFERRED EMBODIMENT(S)

Figure 1:
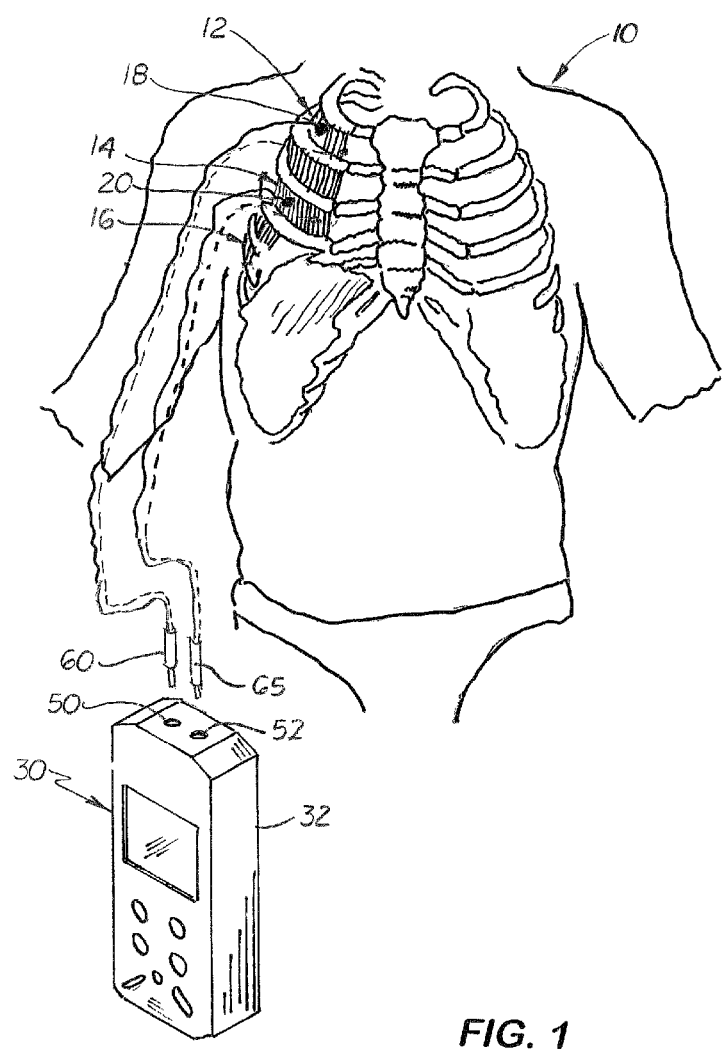
FIG. 1 is an illustration of a patient showing the sleep apnea device attached to electrodes mounted externally on a patient's chest over the first and third intercostals.
Figure 2:
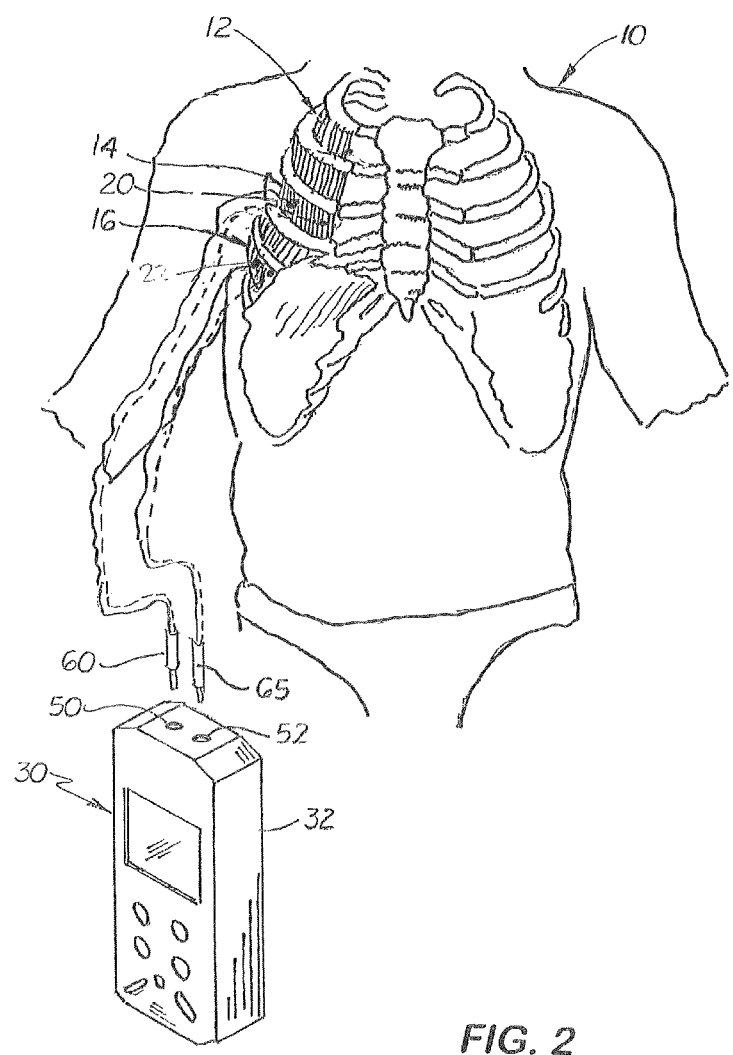
FIG. 2 is an illustration of a patient showing the sleep apnea device attached to electrodes mounted externally on the patient's chest over the right side third and fifth intercostals FIG. 3. is an illustration of two electrical wires each including a cathode electrode and an anode electrodes being positioned over the first, third and fifth intercostals.
Figure 3:
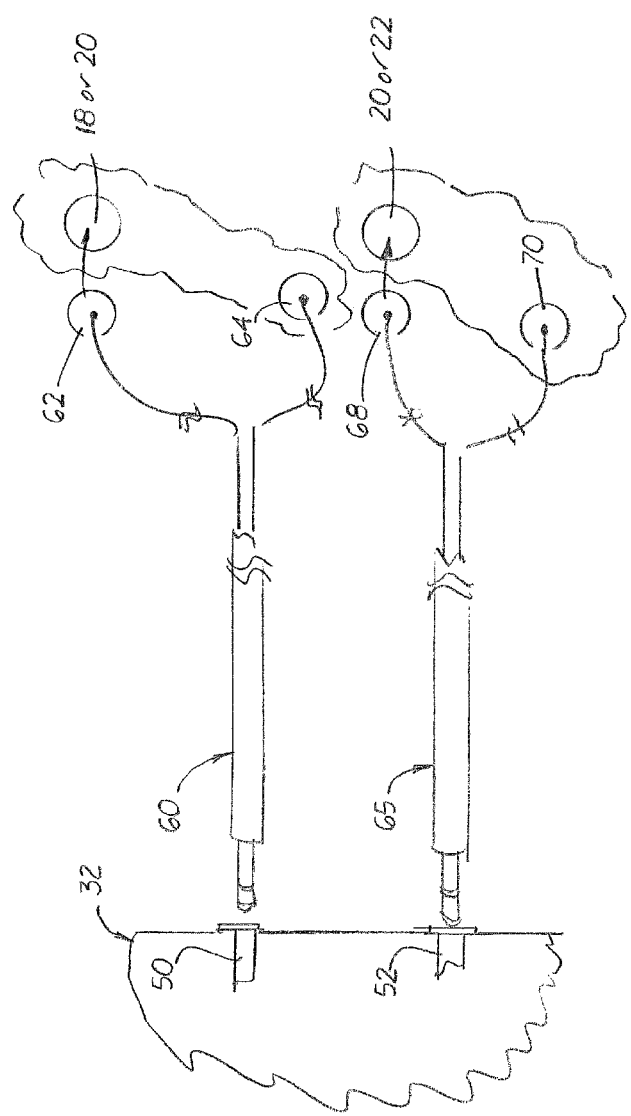

Referring to the FIGS. 1-6, there is shown an individual 10 that suffers from sleep apnea. Mounted over the right side first intercostals 12, the third intercostals 14 and the fifth intercostals 16 are skin electrodes 18, 20 and 22 respectively. 38. During use, the heathcare worker selects the first intercostals 12 and the third intercostals 14 and attaches skins electrodes 18 and 20 thereover (shown in FIG. 1), or selects the third intercostals 14 and the fifth intercostals 16 and attaches to adhesive skin electrodes 20 and 22, thereover (shown in FIG. 2).

Once the pair of intercostals 12 and 14, or 14 and 16 is selected and the skin electrodes 18, 20 or 22 are attached, the two electrode wires 60 and 65 are then connected to the two channel ports 50, 52, on the stimulator's outer housing 32. Each electrode wire 60, 65 and includes a cathode connector 62, 68, respectively, and an anode connector 64, 70 respectively. During setup, the cathode connector 62 and 68 are selectively attached to the two skin electrodes 18 and 20 or 20 and 22. The anode connector 64, 70 for each contact wire 60, 66, respectively, are connected to the skin located directly over the selected intercostals 12 and 14 or 14 and 16 to a second skin electrode (not shown). The anode connectors 64, 70 are spaced apart from the cathode connector 62, 68 and located along the intercostals so that contraction occurs in the intercostals when an electrical pulse is applied thereto.

The electrical simulator 30 that includes an outer housing 32 with a PCB 34 and a battery pack 95 mounted therein. Formed on the PCB 34 are two electrical stimulating channels 36, 38 that are connected in a parallel manner to simultaneously provide an electrical pulse 100 to connect each channel port 50, 52, respectively Mounted on the outer housing 32 and electrically connected to the PCB 34 is a main power switch 40, a main power timer switch 42, two voltage or amplitude control switches 44, 46, two channel electrode wire ports 50, 52, an LCD display 80, an adjustable delay timer switch 85, and an amplitude lock switch 90.

In the preferred embodiment, the stimulator 30 is very similar to the neuromuscular electrical stimulator (known as a NMES) used in the treatment of dysphagia sold by Chattanooga Group of Hixson, Tenn. under the trademark VITAL-STIM. Such an electrical stimulator includes a main power switch 40, a main power timer switch 42, two amplitude control switches 44, 46 coupled to each channel circular assembled on the an internal PCB, two channel electrode wire ports 50, 52 connected to each channel 36, 38, an LCD display 80, an adjustable delay activation switch 85, and an amplitude lock switch 90.

Figure 4:
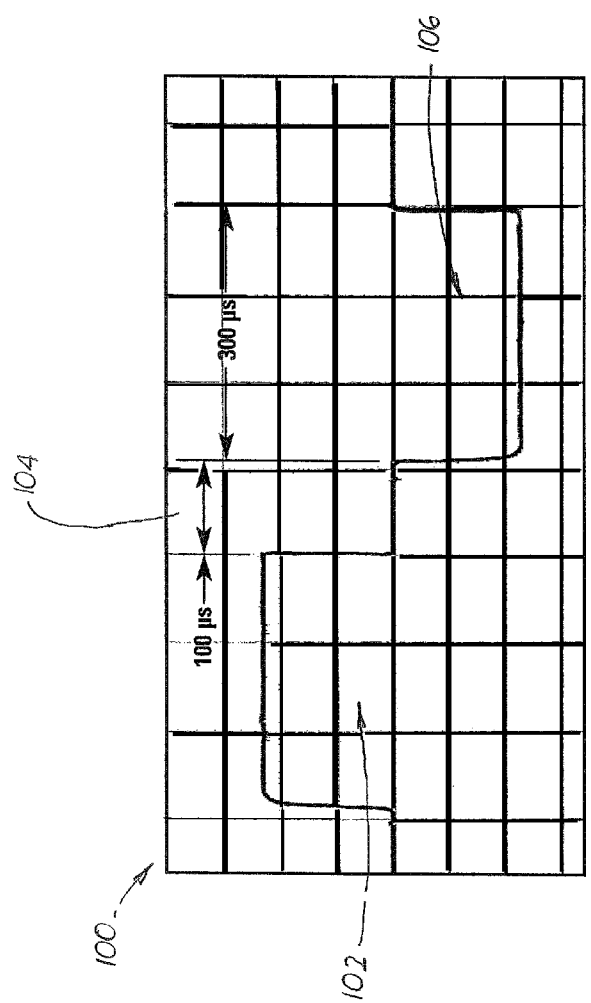
FIG. 4. is an illustration showing the electrical stimulation pattern of a pulse produced by the electrical stimulator.
Figure 5:
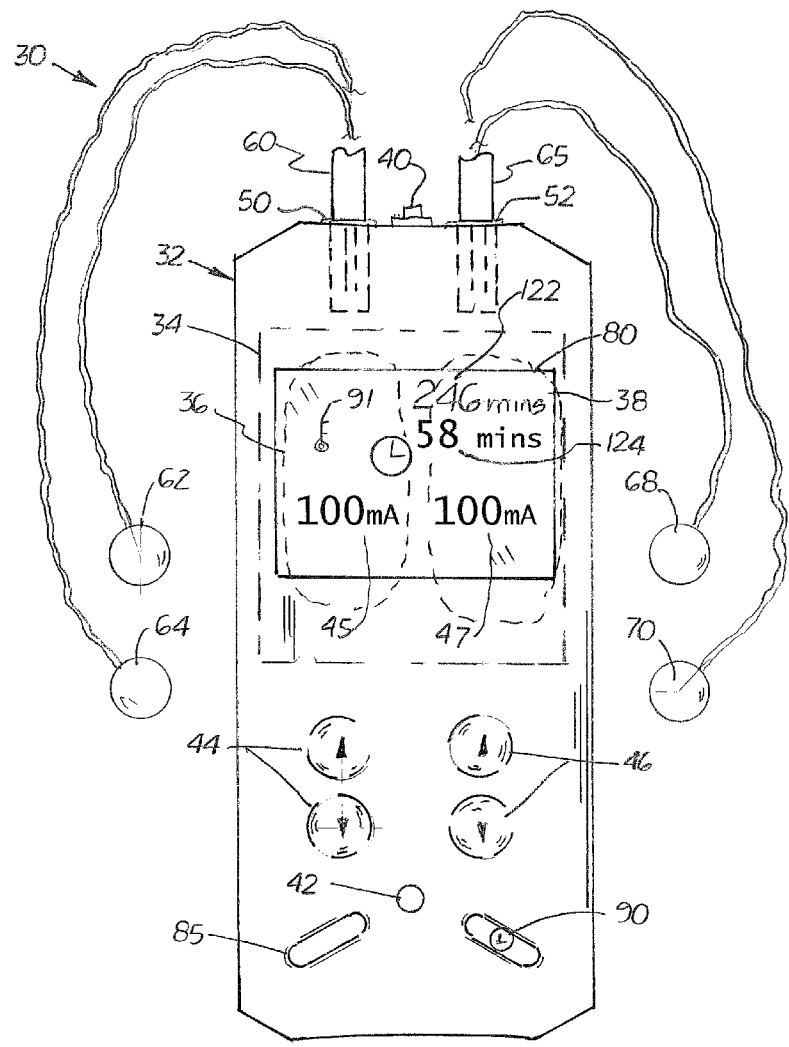
FIG. 5 is a front plan view of the electrical stimulator control unit
Figure 6:
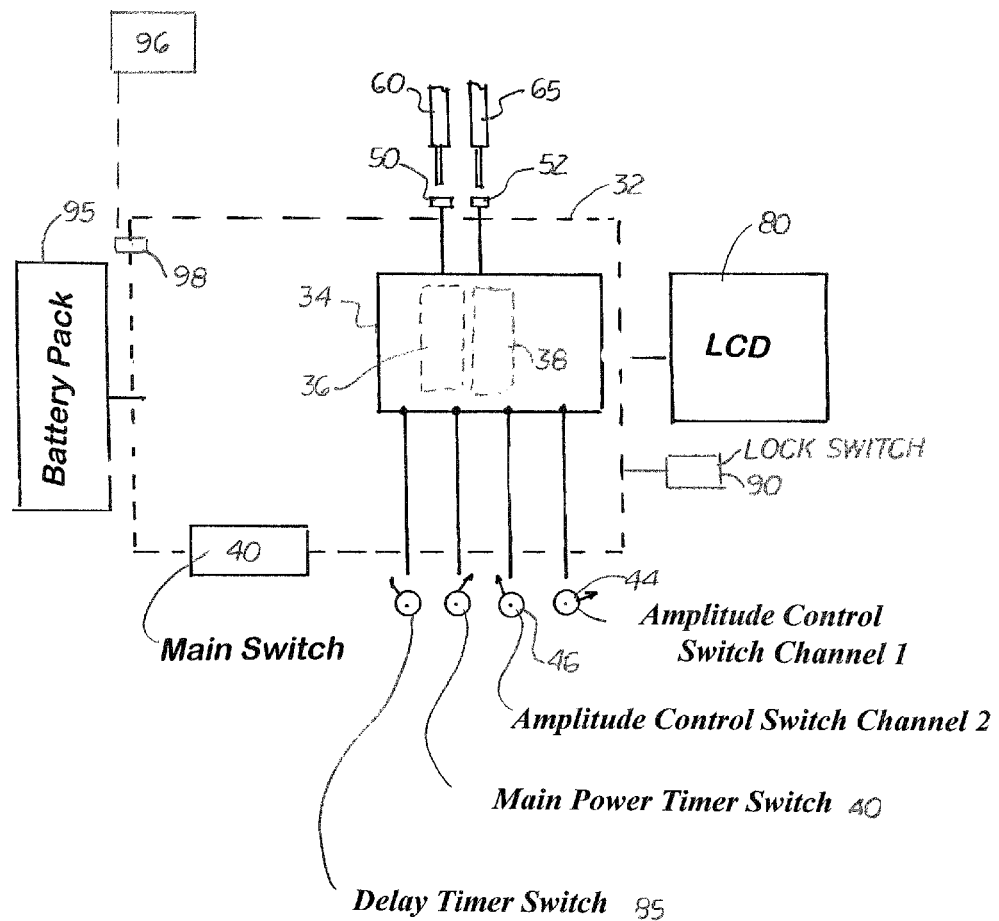
FIG. 6 is a simple electrical diagram showing the components that make up the circuit in the electrical stimulator

FIG. 4 is an illustration showing the stimulating biphasic pulse 100 produced at regular intervals with a total duration of approximately 700 milliseconds. Each phase 102, 106 lasts approximately 300 milliseconds and the interphase 104 lasts approximately 100 milliseconds. The amount of elapsed time between pulses 100 is between 100 to 400 milliseconds.

Prior to dispensing the stimulator 30 to the patient, nerve and muscular tests are conducted to determine the electrical conduction and contraction properties of the first, third and fifth intercostals. From these tests, either the first and third intercostals 12, 14, respectively, are selected or the third and fifth intercostals 14, 16, respectively, are selected. During the tests, the required amplitude (5 to 25 milliamps) needed to cause contraction is determined. Once the tests are completed, the desired pair of intercostals 12 and 14, or 14 and 16 is determined, each intercostals is assigned to one of the channels 36, 38. The desired amplitude is then entered and locked into the stimulator 32 using the two amplitude control switches 44, 46 and the amplitude lock switch 90. The amperage values 45, 47 (in mA) and lock and unlock icons 91 are shown on the LCD display 80.

When activated, the stimulator 32 continuously provides pulses for 59 seconds and then rests for 4 seconds. The stimulation cycle of 59 seconds ON and 4 seconds OFF is repeated throughout the selected sleep period.

During setup, the patient also determines the duration of the sleep period (1, 2, 4, 6 or 8 hrs) and sets the main power timer switch 42 to the sleep period so that the stimulator 30 operates continuously throughout the sleep period. In the preferred embodiment, switch 42 is a display touch switch that enables the patient to press and manually toggle through different time periods. In the preferred embodiment, the time periods are 1 hour, 2, hours, 4 hours, 6 hours or 8 hours. During use, the selected time value 122 is presented on the LCD display 80. The patient also adjusts the delay activation switch 85 which is also a display touch switch to set the time the stimulator 30 begins to created pulses 100. In the preferred embodiment, the amount of time delay is 10, 20, 30, 45 or 60 mins. The selected delay time value 124 is also presented on the LCD display 80.

In the preferred embodiment, the stimulator 30 includes a battery pack 95 contains two AA 1.5 volt batteries. It should be understood however, the battery pack 95 may be replaced by a 115 volt AC-DC adaptor that selectively connects to the stimulator 30 via a plug 98.

After the main power timer switch 42 and the delay activation switch 85 are set to the desired times, the main power timer switch 40 is then activated.

Using the above described device a method for treating sleep apnea is provided comprising the following steps:

a. locating externally the location of first, third and fifth intercostals on the right side of the chest of a patient experiencing sleep apnea;

b. externally testing the electrical conductivity of said first, third and fifth intercostals;

c. selecting an electrical stimulator with two channels that generate a biphasic pulse which when applied to said first, third or fifth intercostals, causes contraction, said stimulator, a main power switch and a main timer switch that determines how long said stimulator generates biphasic pulses, and a delay activation switch that controls when said stimulator begins generating biphasic pulses after said main power switch is activated;

d. adjusting said amplitude control switches assigned to each said channel according to said electrical conductivity tests;

e. connecting an electrode wire to each said channel, each said electrode wire includes a cathode connector and an anode connector;

f. attaching said cathode connector and said anode connector from one said electrode wire to over said third intercostals and attaching said cathode connector and said anode connector from the other said electrode wire to over said first intercostals or said fifth intercostals;

g. adjusting said timer switch to select different lengths of sleep periods;

h. adjusting said delay activation switch to set the time said stimulator begins generating said pulses; and, i. activating said main power switch;

In compliance with the statute, the invention described herein has been described in language more or less specific as to structural features. It should be understood, however, that the invention is not limited to the specific features shown, since the means and construction shown is comprised only of the preferred embodiments for putting the invention into effect. The invention is therefore claimed in any of its forms or modifications within the legitimate and valid scope of the amended claims, appropriately interpreted in accordance with the doctrine of equivalents.

I claim:

1. A device for treating a patient experiencing episodes of sleep apnea during a designated sleep period by stimulating the first and third intercostals or third and fifth intercostals of the patient, said device comprising:

at least two electrode wires each with a cathode connector and an anode connector;

an electrical stimulator configured to repeatedly produce an electrical pulse with a magnitude of 5 to 25 milliamps for 59 seconds on, 4 seconds off;

said electrical stimulator includes:
at least two channels, each connected to one said electrode wire;
at least one amplitude control switch that is configured to adjust the amplitude of said electrical pulse produced by said electrical stimulator;
a timer switch configured to select different sleep periods;
a delay activation switch configured to select a time to first begin to produce electrical pulses; and
a main power switch; and at least two pairs of electrodes, each electrode pair connected to said anode connector and said cathode connector of said at least two electrode wires, respectively;

wherein said at least two pairs of electrodes are adapted to be placed over said first and third intercostals or said third and fifth intercostals, respectively; and the electrical pulse is delivered during at least one of said different sleep periods in order to prevent apnea during at least one of said different sleep periods.

2. The device as recited in claim 1, wherein said electrical stimulator further includes a LCD display that is configured to display to the patient said amplitude, said different sleep periods, said time to first being to produce electrical pulses.

3. The device as recited in claim 1, wherein said electrical stimulator is battery operated.

4. A method for treating sleep apnea, comprising the following steps:

a. locating externally the location of first, third, and fifth intercostals on the right side of the chest of a patient experiencing sleep apnea;

b. externally testing the electrical conductivity of said first, third and fifth intercostals;

c. providing an electrical stimulator, said electrical stimulator includes:
two electrode wires each with a cathode connector and an anode connector;
two channels, each connected to one said electrode wire;
two pairs of electrodes, each electrode pair connected to said anode connector and said cathode connector of the two electrode wires, respectively;
an amplitude control switch assigned to each of the two channels that adjusts an amplitude of said electrical pulse produced by said electrical stimulator;
a timer switch that selects different sleep periods;
a delay activation switch that selects a time to first begin to produce electrical pulses; and
a main power switch;

d. adjusting the amplitude within a range of 5 to 25 milliamps using said amplitude switch assigned to each of the two channels according to electrical conductivities determined in step (b);

e. attaching one pair of the two electrode pairs over said third intercostals and attaching the other pair of the two electrode pairs over said first intercostals or said fifth intercostals;

f. adjusting said timer switch to select different lengths of sleep periods;

g. adjusting said delay activation switch to set the time said stimulator begins generating said pulses; and, h. preventing apnea of the patient by activating said main power switch on said stimulator to repeatedly stimulate the patient with sleep apnea with a biphasic pulse having an amplitude between 5 and 25 milliamps, an on period of 59 seconds and an off period of 4 seconds, said pulse begins according to said delay activation switch and continues for a sleep period according to said timer switch.

* * * * *